(12) United States Patent
Wang

(10) Patent No.: US 9,629,538 B2
(45) Date of Patent: Apr. 25, 2017

(54) CONTOUR INTEGRATION PERIMETRY VISION TEST

(71) Applicant: VITAL ART AND SCIENCE, LLC, Richardson, TX (US)

(72) Inventor: Yi-Zhong Wang, Frisco, TX (US)

(73) Assignee: VITAL ART AND SCIENCE, LLC, Richardson, TX (US)

(*) Notice: Subject to any disclaimer, the term of this patent is extended or adjusted under 35 U.S.C. 154(b) by 0 days.

(21) Appl. No.: 14/785,807

(22) PCT Filed: Apr. 15, 2014

(86) PCT No.: PCT/US2014/034105
§ 371 (c)(1),
(2) Date: Oct. 20, 2015

(87) PCT Pub. No.: WO2014/176070
PCT Pub. Date: Oct. 30, 2014

(65) Prior Publication Data
US 2016/0089017 A1     Mar. 31, 2016

Related U.S. Application Data

(60) Provisional application No. 61/816,421, filed on Apr. 26, 2013.

(51) Int. Cl.
*A61B 3/02*     (2006.01)
*A61B 3/032*    (2006.01)
(Continued)

(52) U.S. Cl.
CPC ............ *A61B 3/032* (2013.01); *A61B 3/0091* (2013.01); *A61B 3/024* (2013.01)

(58) Field of Classification Search
USPC ................................................ 351/200–246
See application file for complete search history.

(56) References Cited

U.S. PATENT DOCUMENTS 4,971,434 A * 11/1990 Ball ........................ A61B 3/032
                                                    351/224
6,656,131 B2    12/2003 Alster et al.
(Continued)

FOREIGN PATENT DOCUMENTS

CN      101742958 A     6/2010
CN      201929941 U     8/2011
(Continued)

OTHER PUBLICATIONS

International Search Report and Written Opinion of the International Searching Authority, Application No. PCT/US2014/034105, dated Jul. 28, 2014, 16 pages.

*Primary Examiner* — Mohammed Hasan

(57) ABSTRACT

One aspect of the disclosure includes a method to assess vision function. In one embodiment, the method comprises providing a sequence of test images on a display (106) to a test subject (102) during a stimulus interval and providing a response pattern image for each of the sequence of test images during a response interval after the stimulus interval. Each of the sequence of test images includes multiple stimulus patterns (304, 306) arranged around a fixation target (302). The response pattern image includes multiple response targets (320), each of which corresponds to a location of each of the multiple stimulus patterns (304, 306). One (304) of the multiple stimulus patterns (304, 306) differs. An assessment of a vision function of the test subject (102) is based on a selection by the test subject of one of the multiple response targets (320) that the test subject indicates corresponds to a location of the multiple stimulus pattern that differs (304). A corresponding vision testing system (100) is disclosed as well.

20 Claims, 13 Drawing Sheets

(51) Int. Cl.
*A61B 3/024* (2006.01)
*A61B 3/00* (2006.01)

(56) References Cited

U.S. PATENT DOCUMENTS

| | | |
|---|---|---|
| 7,220,000 B2 | 5/2007 | Alster et al. |
| 7,275,830 B2 | 10/2007 | Alster et al. |
| 7,665,847 B2 | 2/2010 | Alster et al. |
| 8,066,376 B2 * | 11/2011 | Wang .................. A61B 3/032 |
| | | 351/205 |
| 9,039,182 B2 | 5/2015 | Huang |
| 2005/0018132 A1 * | 1/2005 | Fukuma ................ A61B 3/103 |
| | | 351/200 |
| 2008/0204662 A1 | 8/2008 | Kanazawa et al. |
| 2011/0007267 A1 | 1/2011 | Erickson et al. |
| 2012/0050685 A1 | 3/2012 | Bartlett et al. |

FOREIGN PATENT DOCUMENTS

| | | |
|---|---|---|
| CN | 102458220 A | 5/2012 |
| CN | 102686146 A | 9/2012 |
| CN | 102727171 A | 10/2012 |
| WO | 9816150 A1 | 4/1998 |
| WO | 9952419 A1 | 10/1999 |
| WO | 2014176070 A1 | 10/2014 |

* cited by examiner

# CONTOUR INTEGRATION PERIMETRY VISION TEST

CROSS-REFERENCE TO RELATED APPLICATION

This application is the National Stage of, and therefore claims the benefit of, International Application No. PCT/US2014/034105 filed on Apr. 15, 2014, entitled "CONTOUR INTEGRATION PERIMETRY VISION TEST," which was published in English under International Publication Number WO 2014/176070 on Oct. 30, 2014. International Application No. PCT/US2014/034105 claims priority to U.S. Provisional Application No. 61/816,421 filed on Apr. 26, 2013. Both of the above applications are commonly assigned with this National Stage application and are incorporated herein by reference in their entirety.

TECHNICAL FIELD OF THE INVENTION

The present invention is directed, in general, to vision testing and, more specifically, to vision testing using a sequence of images.

BACKGROUND OF THE INVENTION

In U.S. Pat. No. 8,066,366, entitled "Dynamic Shape Discrimination Vision Test," Wang and Krenik teach vision tests based on dynamic images that are viewed by a test subject, who makes responses based on their perception of the dynamic images. Computer analysis of the responses made allows the test subject's vision function to be determined. The benefits of a low-cost computerized system such as the work of Wang and Krenik are clear to those skilled in the art. Monitoring vision function is critically important for persons with a wide range of vision disorders. In particular, persons with retinal disease may benefit from ongoing vision monitoring to ensure that changes in their vision function, which may signal serious medical conditions needing prompt attention, are not going unnoticed.

SUMMARY OF THE INVENTION

One aspect of the disclosure includes a method to assess vision function. In one embodiment, the method comprises providing a sequence of test images on a display coupled to a computer to a test subject during a stimulus interval and providing a response pattern image on the display to the test subject for each of the sequence of test images during a response interval after the stimulus interval. Each of the sequence of test images includes multiple stimulus patterns arranged around a fixation target. The response pattern image includes multiple response targets, each of which corresponds to a location of each of the multiple stimulus patterns. At least one of the multiple stimulus patterns differs from others of the multiple stimulus patterns. An assessment of a vision function of the test subject is based at least partially on a selection by the test subject during the response interval, for each of the sequence of test images, of at least one of the multiple response targets of the response pattern image that the test subject indicates corresponds to a location of the at least one of the multiple stimulus patterns that differs from others of the multiple stimulus patterns.

Another aspect of the disclosure includes a vision testing system. In one embodiment, the vision testing system comprises a display and a computer coupled to the display. The computer is configured to display to a test subject a sequence of test images during a stimulus interval and a response pattern image for each of the sequence of test images during a response interval after the stimulus interval. Each of the sequence of test images includes multiple stimulus patterns arranged around a fixation target. The response pattern image includes multiple response targets, each of which corresponds to a location of each of the multiple stimulus patterns. At least one of the multiple stimulus patterns differs from others of the multiple stimulus patterns. An assessment of a vision function of the test subject is based at least partially on a selection by the test subject during the response interval, for each of the sequence of test images, of at least one of the response patterns of the response pattern image that the test subject indicates corresponds to a location of the at least one of the multiple stimulus patterns that differs from others of the multiple stimulus patterns.

The foregoing has outlined preferred and alternative features of the present invention so that those skilled in the art may better understand the detailed description of the invention that follows. Additional features of the invention will be described hereinafter that form the subject of the claims of the invention. Those skilled in the art should appreciate that they can readily use the disclosed conception and specific embodiment as a basis for designing or modifying other structures for carrying out the same purposes of the present invention. Those skilled in the art should also realize that such equivalent constructions do not depart from the spirit and scope of the invention.

BRIEF DESCRIPTION OF THE DRAWINGS

For a more complete understanding of the present invention, reference is now made to the following descriptions taken in conjunction with the accompanying drawings, in which.

DETAILED DESCRIPTION

This disclosure provides additional vision tests beyond those provided in U.S. Pat. No. 8,076,366, entitled "Dynamic Shape Discrimination Vision Test." In particular, this disclosure teaches vision tests based on a test subject's ability to integrate vision information from contour segments and detect distortion across regions of the retina in which a contour is visible in the course of testing.

Figure 1:
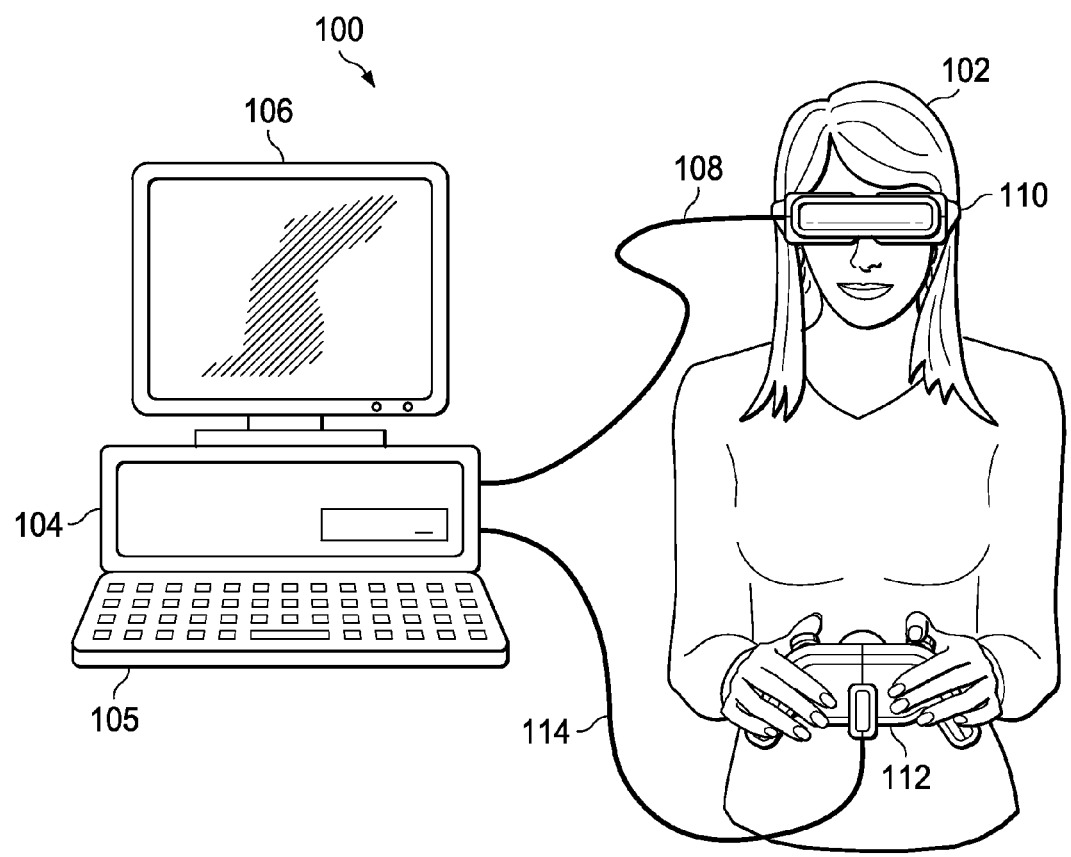
FIG. 1 illustrates a test subject undergoing a computerized vision test.

In FIG. 1, a test subject 102 of a computerized vision testing system 100 is shown wearing a binocular viewer 110 connected by a display electrical cable 108 to a computer 104. The computer 104 generates a series of test images that are viewed on the binocular viewer 110 by the test subject 102 and, depending on how the test subject 102 discerns the test images, the test subject 102 provides feedback through a game controller 112. The test subject may also provide feedback through a keyboard 105 and might also directly view test images on a conventional computer monitor 106. Game controller 112 is connected to computer 104 via cable 114.

Figure 2:
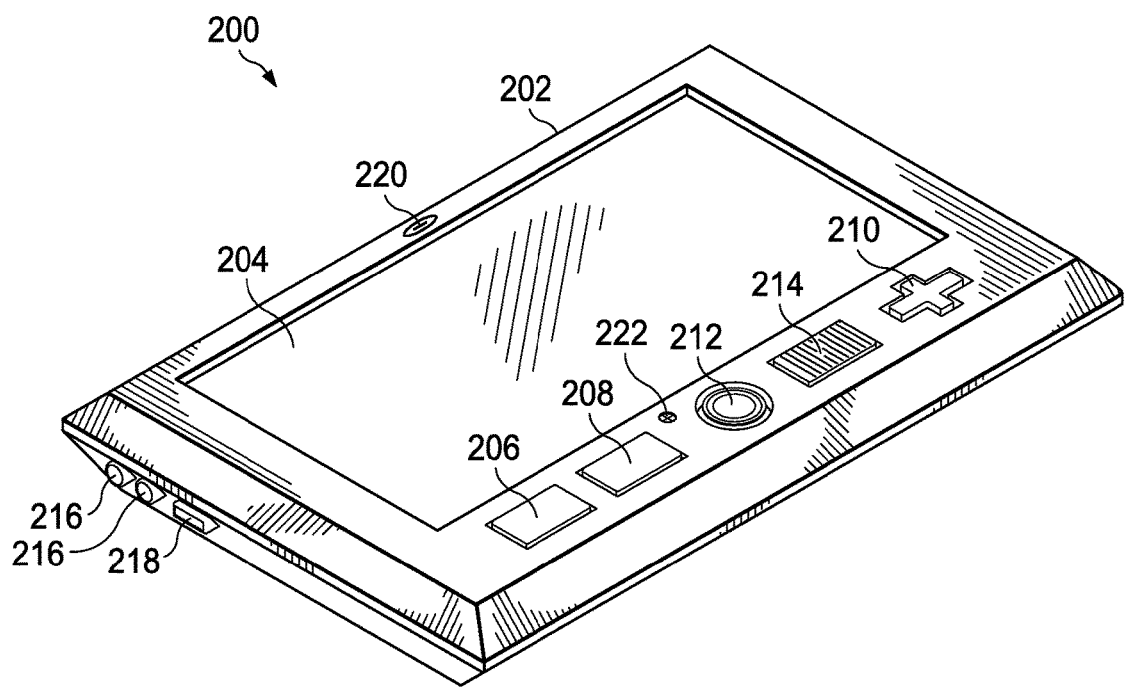
FIG. 2 illustrates a handheld computer device including a touch screen display.

In FIG. 2, a handheld device 200 is shown. Handheld device 200 includes touch screen display 204, casing 202, cursor control 210, fingerprint sensor 214, camera 212, microphone 222, first button 206, second button 208, communications interface 218, power interface 216, and speaker 220.

Computerized vision testing system 100 and handheld device 200 are included in this disclosure to provide examples of systems over which a computerized vision test may be delivered. As this disclosure teaches novel test images and response images, it will be clear to those skilled in the art that the test images and response images of this disclosure may be delivered over systems such as computerized vision testing system 100 or handheld device 200. A test subject such as test subject 102 may respond to test images or response images delivered in the course of a computerized vision test over a binocular viewer 110, a conventional computer display 106, a touch screen display 204, or any other type of electronic display suitable for vision testing. And a test subject may deliver feedback based on use of a game controller 112, keyboard, 105, touch screen display 204, or any other possible user input or feedback device (e.g., joysticks, eye tracking systems, voice response systems, track balls, a computer mouse, and gesture recognition devices, are a few examples of the many possible user input devices that may be utilized). For the purpose of this disclosure, it will be recognized that the vision tests taught may be delivered over any suitable computer device including an electronic display and an input device that are suitable for such use. The explanations of the embodiments provided will assume the use of a handheld device 200 including a touch screen display 204. Those skilled in the art will recognize that utilization of other electronic displays and input devices may be adopted through minor and conventional extensions of the embodiments provided.

Figure 3A:
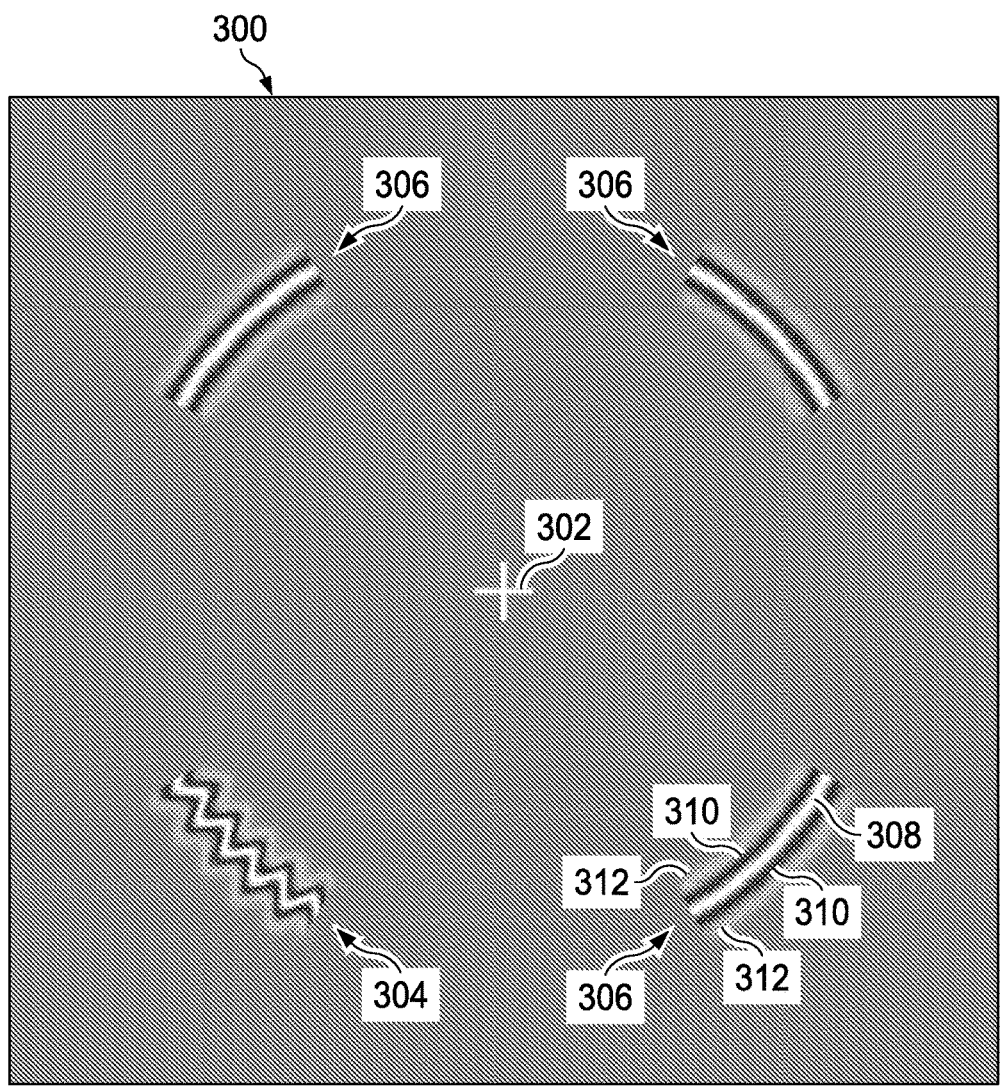
FIG. 3a illustrates an embodiment of a test image including a fixation target and four stimulus patterns.

FIG. 3a shows an embodiment of a test image including a fixation target 302, three smooth arcs 306, and a modulated arc 304. The modulated arc 304 is in the lower left quadrant of the test image. The test image of FIG. 3a is presented on a gray background 300. Throughout this disclosure, test images are shown that include a fixation target 302. Those skilled in the art will recognize that many possible fixation targets are possible in addition to the cross shown for fixation target 302. Cross hairs, small circles, dots, and other possible objects may be used for fixation targets as are commonly used in vision testing. Those skilled in the art will further recognize that fixation targets may be of different colors and may also be dynamic and may flash, rotate, oscillate, or otherwise include motion to augment the ability of a test subject to fixate on them.

Throughout this disclosure, test images will be shown in grayscale on a gray background 300. However, those skilled in the art will recognize that colored backgrounds and colored test images are also possible and that use of color may enhance some aspects of vision testing for some embodiments. Test images are shown as square images, but those skilled in the art will recognize that rectangular images or other formats are also possible. In particular, test images corresponding to the aspect ratios of the electronic displays they are delivered over may be beneficial for some embodiments.

It is assumed that a test subject may test one eye at a time or may test both eyes together with various embodiments of vision tests that are embodied herein. Other aspects of vision testing, such as maintaining acceptable distance from an electronic display on which test images are displayed, maintaining appropriate levels of ambient lighting, maintaining appropriate levels of display contrast and brightness, and other factors affecting vision testing may be accounted for consistently with presently known techniques and best practices.

Contours utilized for test images are embodied as smooth arcs 306 and as modulated arcs 304 that are distributed radially about a fixation target 302. However, many other contours may be utilized with similar effect including line segments, arbitrary curves, various wavy contours, and many other possible contours. Closed shapes such as ellipses, circles, triangles, and other closed shapes may also be distributed about a fixation target 302 in the place of contours. As will be explained with regard to FIG. 5, such contours may be of various sizes, may be of various cross-section widths and luminance profiles, may be distributed about a fixation target at various angles, and may be at various distances about a fixation target. Some of the contours used may be modulated along a contour length such as modulated arc 304. In such cases, modulation may be sinusoidal, triangular, saw tooth, square, or other possible types of spatial modulation. Frequency and amplitude of modulation along the contour length may be varied for various embodiments.

The smooth arcs 306 and modulated arc 304 of FIG. 3a include a central bright region 308, surrounding dark regions 310 on each side of central bright region 308, and outer light regions 312 on the outer sides of surrounding dark regions 310. This variation in brightness across the width of a contour is referred to as cross-sectional luminance modulation. The width, brightness, grayscale, color, and other aspects of central bright region 308, surrounding dark regions 310 and outer light regions 312 may be varied in some embodiments. Those skilled in the art will recognize that many different cross-sectional luminance modulations are possible for various embodiments, including cross-sectional luminance modulations that vary linearly, vary abruptly, vary exponentially, vary using other mathematical functions, vary with combinations of mathematical functions, are made up of various numbers of stripes of varying luminance, or vary in other possible ways. Also, it is noted that the smooth arcs 306 and modulated arc 304 of FIG. 3a are embodied as somewhat fuzzy elements as if they are somewhat out of focus (as opposed to clearly and highly defined contours). This use of fuzzy images for visual stimulus patterns is intentional as it forces a test subject to integrate the response of the photo detectors in their retina to discern a contour. Those skilled in the art will recognize that a wide range of images that have varying levels of fuzziness and that are made up of various numbers of lighter and darker regions (these regions may be stripes as shown in FIG. 3a or may be regions formed in other shapes or contours) and may use a wide range of cross-sectional luminance modulations are possible for various embodiments.

Figure 3B:
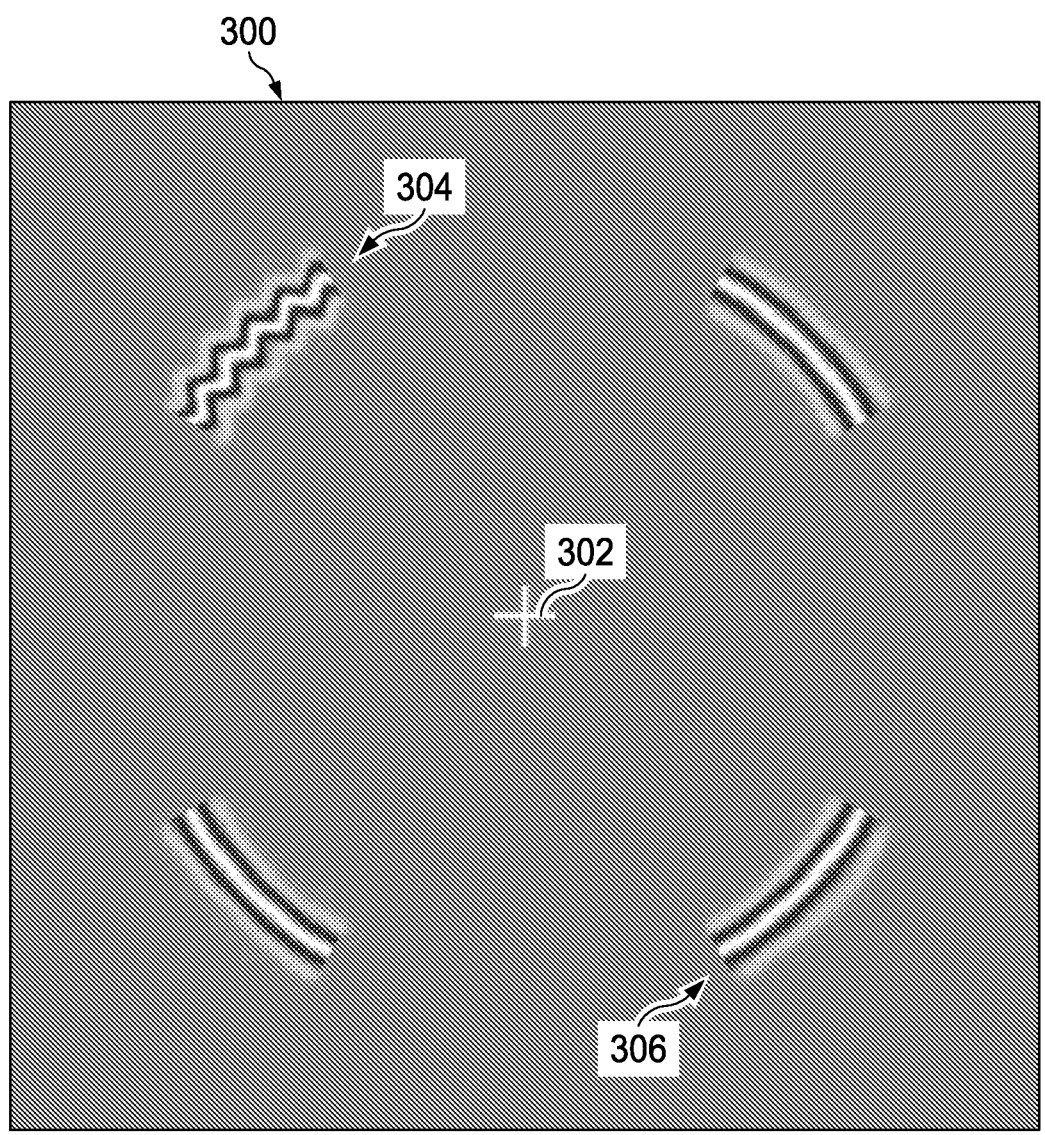
FIG. 3b illustrates another embodiment of a test image including a fixation target and four stimulus patterns.

FIG. 3b shows an embodiment of a test image including a fixation target 302, three smooth arcs 306, and a modulated arc 304. The test image of FIG. 3b is similar to that of FIG. 3a, but the modulated arc 304 has moved to occupy the upper left quadrant and the modulation amplitude is reduced.

Figure 3C:
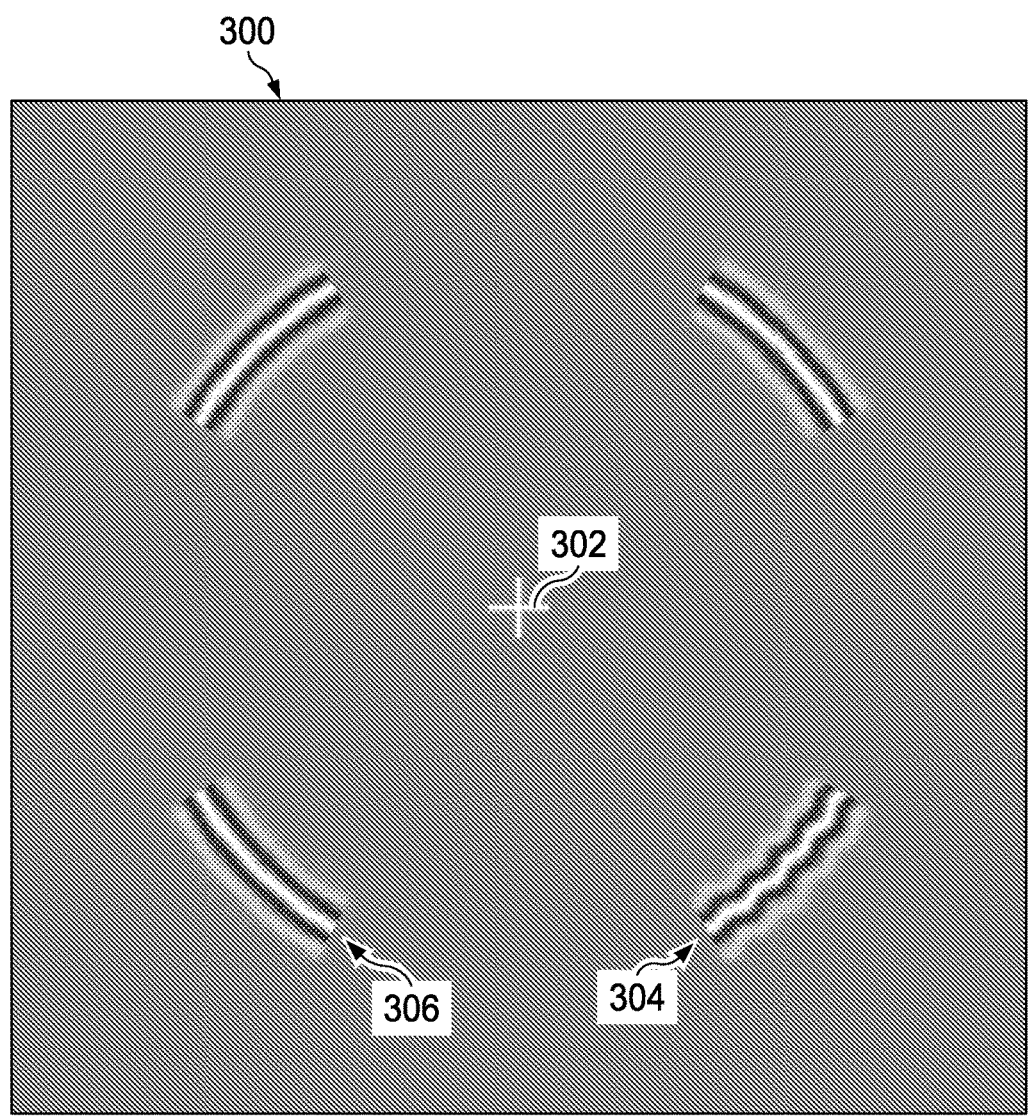
FIG. 3c illustrates another embodiment of a test image including a fixation target and four stimulus patterns.

FIG. 3c shows an embodiment of a test image including a fixation target 302, three smooth arcs 306, and a modulated arc 304. The test image of FIG. 3c is similar to that of FIG. 3b, but the modulated arc 304 has moved to occupy the lower right quadrant and the modulation amplitude is further reduced.

Figure 3D:
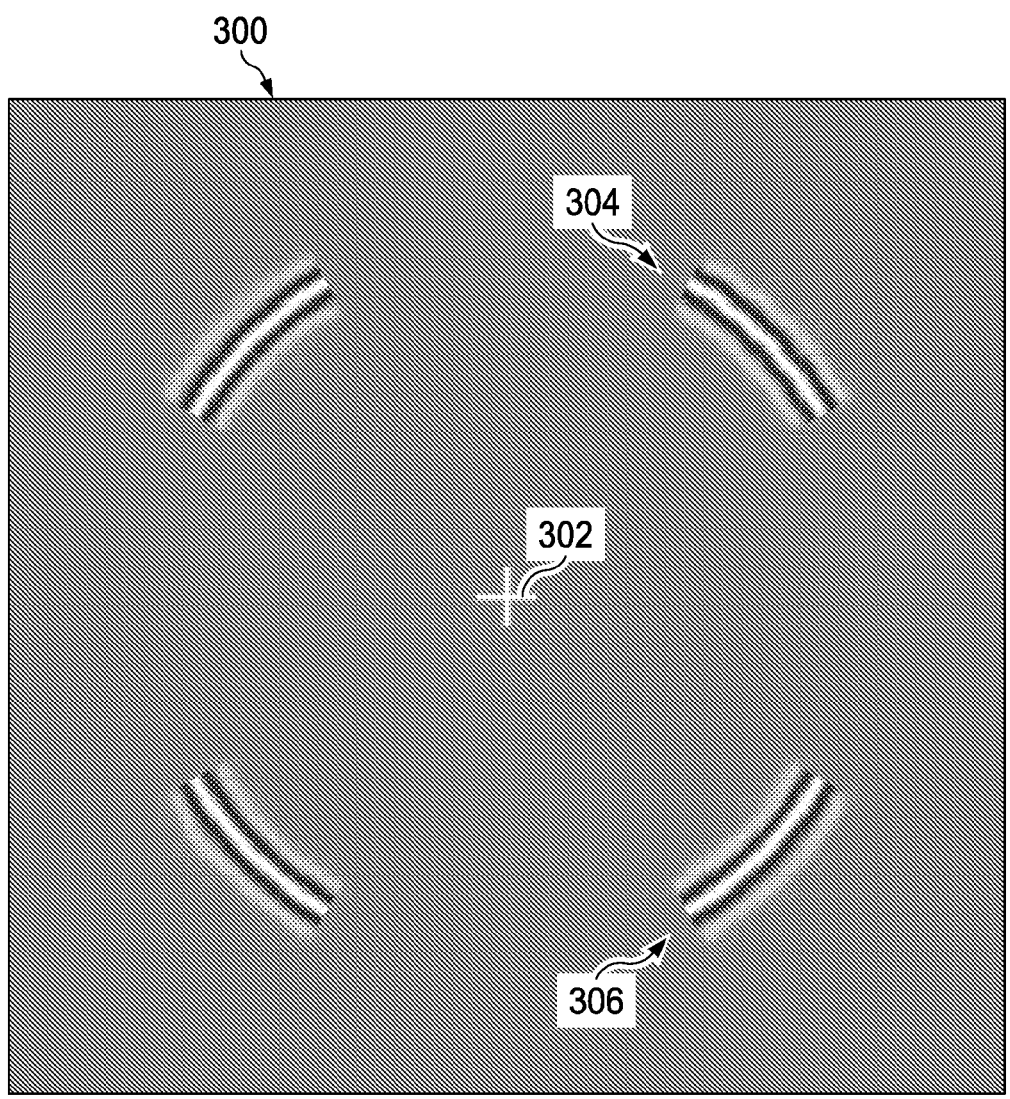
FIG. 3d illustrates another embodiment of a test image including a fixation target and four stimulus patterns.

FIG. 3d shows an embodiment of a test image including a fixation target 302, three smooth arcs 306, and a modulated arc 304. The test image of FIG. 3d is similar to that of FIG. 3c, but the modulated arc 304 has moved to occupy the upper right quadrant and the modulation amplitude is still further reduced.

Figure 3E:
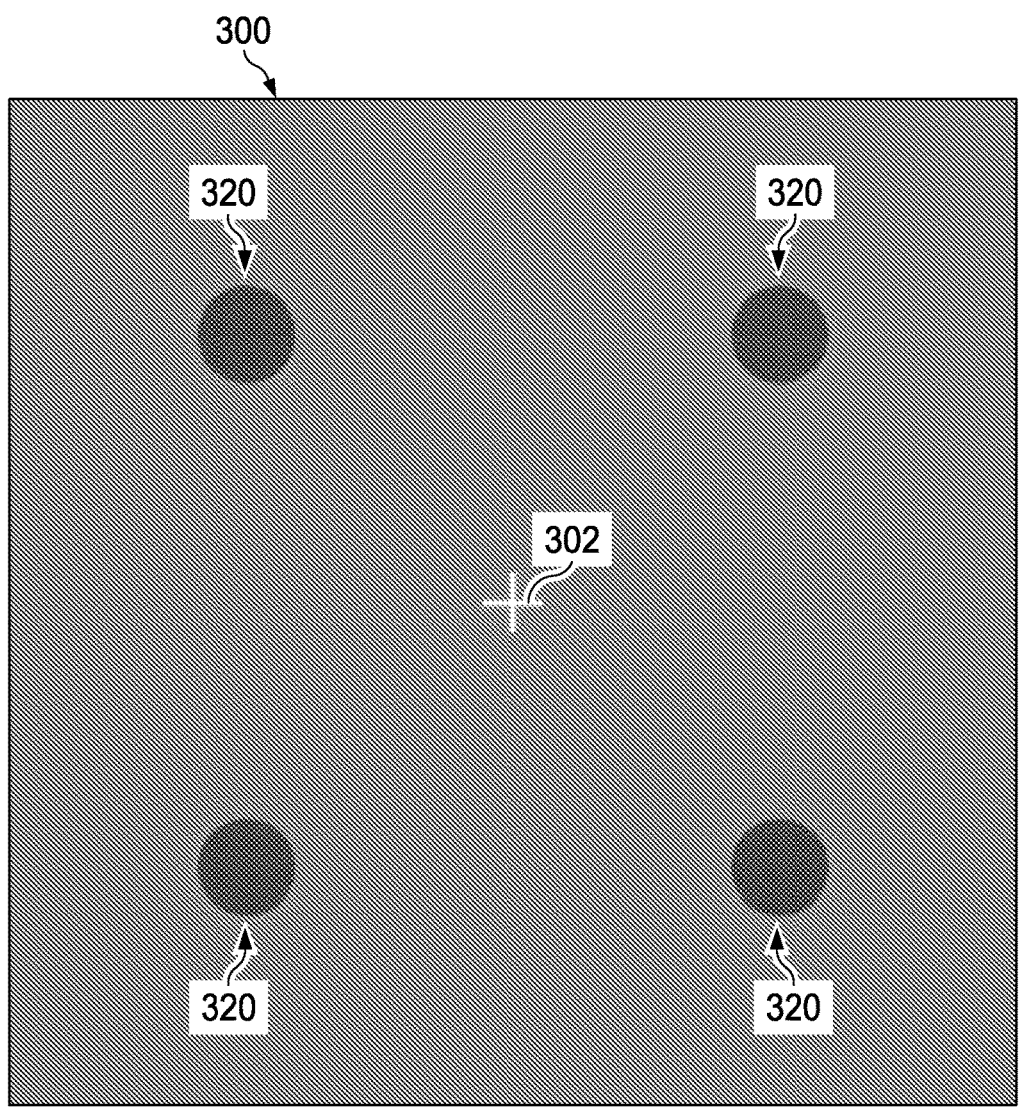
FIG. 3e illustrates an embodiment of a response pattern image suitable for use with the images shown in FIGS. 3a-3d.

FIG. 3e shows an embodiment of a response pattern image suitable for use with the images shown in FIGS. 3a-3d. FIG. 3e includes background 300, fixation target 302, and response targets 320. Response targets 320 are shown as gray dots and are located radially about fixation target 302 to correspond to the locations that smooth arcs 306 and modulated arc 304 occupied in FIGS. 3a-3d. In this fashion, a test subject may detect on a response target 320 during a time interval in which the response pattern of FIG. 3e is displayed to indicate selection of the position in which the modulated arc 304 was just previously displayed. In the course of vision testing utilizing FIGS. 3a-3e, a stimulus interval of time will occur in which one of the test images shown in FIG. 3a-3d will be displayed. During this stimulus interval, a test subject will observe the test image and note the location of the modulated arc 304 while he/she fixates at the fixation target 302. During a second response interval that will follow the stimulus interval, the test subject will be presented with the response pattern of FIG. 3e. During the response interval, the test subject will select (via touch screen or, as previously noted, other input device) the response target that corresponds to the location of the modulated arc 304 that was just previously displayed during the stimulus interval. During the response interval, the test subject doesn't need to fixate at a fixation target and incorporation of a fixation target 302 in a response pattern image is an optional feature.

The stimulus interval may be of varying lengths of time. Generally, times less than 250 milliseconds may be used for some embodiments as times less than 250 milliseconds allow test subjects sufficient time to integrate visual stimulus but does not allow time to stare at or deeply study a test image or make multiple eye movements to search for a modulated contour using their best central vision (best vision). Response intervals may be of convenient lengths of time and may simply end when a test subject makes a selection. If a test subject waits too long to make a selection, the test system may prompt the test subject to make a selection even if they are not sure which target to select. Some test protocols may allow test subjects to guess when they are unsure without ultimately reducing the effectiveness of an overall vision test. Tests are also possible in which stimulus intervals are variable so that the integration time capability of a test subject may be assessed. And tests that utilize stimulus intervals that are adaptive to test subject capability, adaptive to modulated arc 304 modulation amplitude, or other factors are also possible.

In the course of vision testing utilizing FIGS. 3a-3e, multiple trials of stimulus intervals followed by response intervals will be undertaken in sequence. As noted, FIGS. 3a-3d provide various locations and modulation amplitudes of modulated arc 304. In the course of a vision test, modulated arc 304 may appear in these various locations and at various modulation amplitudes so that the ability of a test subject to distinguish the location of modulated arc 304 when it has sufficiently small modulation amplitude so that distinguishing it from smooth arcs 306 is at the limit of the test subject to discern it. In such a fashion, a test subject's visual function may be assessed and objectively scored as a function of the region of their retina. That is, in addition to an overall visual function score, a test subject may also be scored based on the minimum modulation amplitude they could detect in each quadrant of their vision. Those skilled in the art will recognize in addition to the four quadrants used for testing in FIG. 3a-3e, that additional embodiments of similar tests are possible that use more or fewer regions of stimulation.

Figure 4A:
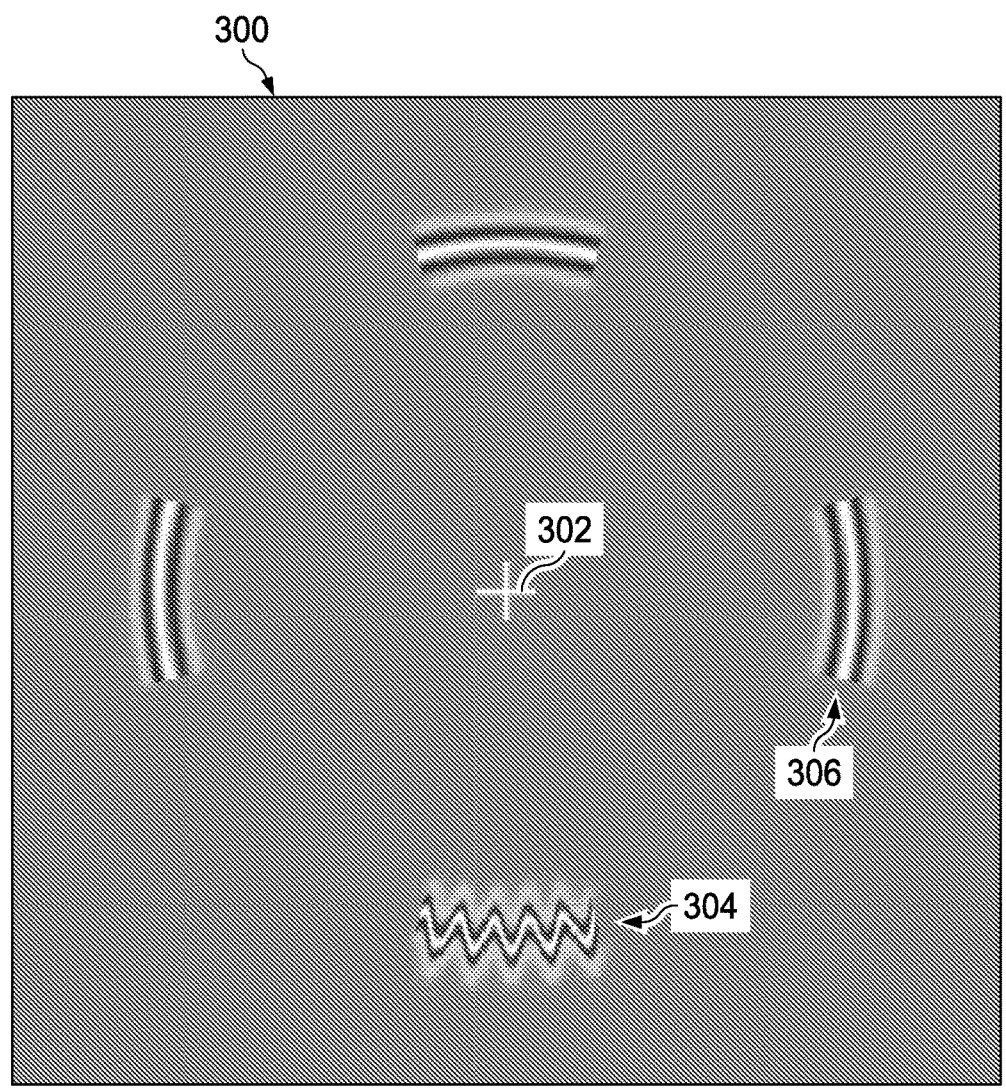
FIG. 4a illustrates another embodiment of a test image including a fixation target and four stimulus patterns.

FIG. 4a shows an embodiment of a test image including a fixation target 302, three smooth arcs 306, and one modulated arc 304. The modulated arc 304 appears directly below the fixation target.

Figure 4B:
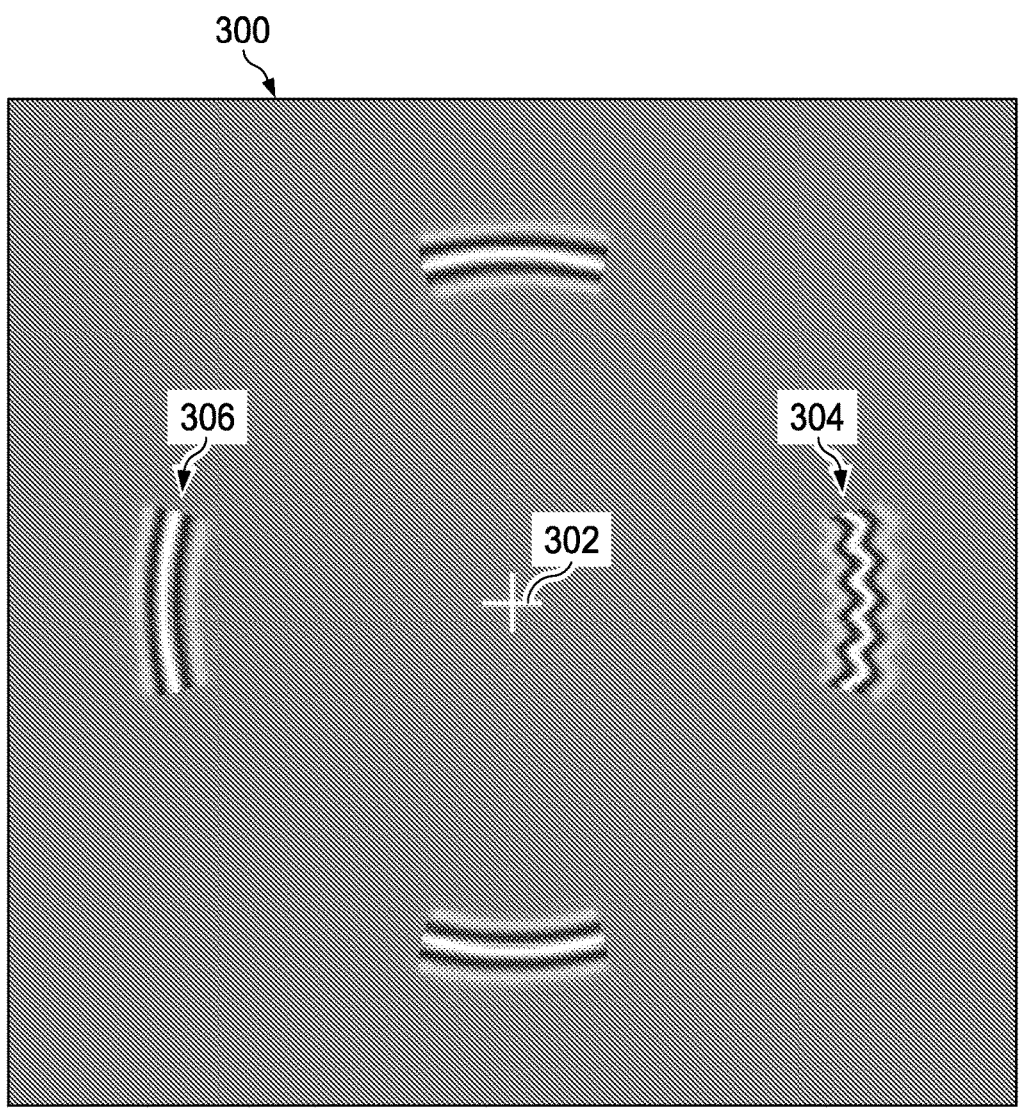
FIG. 4b illustrates another embodiment of a test image including a fixation target and four stimulus patterns.

FIG. 4b shows an embodiment of a test image including a fixation target 302, three smooth arcs 306, and one modulated arc 304. The test image of FIG. 4b is similar to that of FIG. 4a, but the modulated arc 304 has moved to be directly to the right of the fixation target 302 and the modulation amplitude is reduced.

Figure 4C:
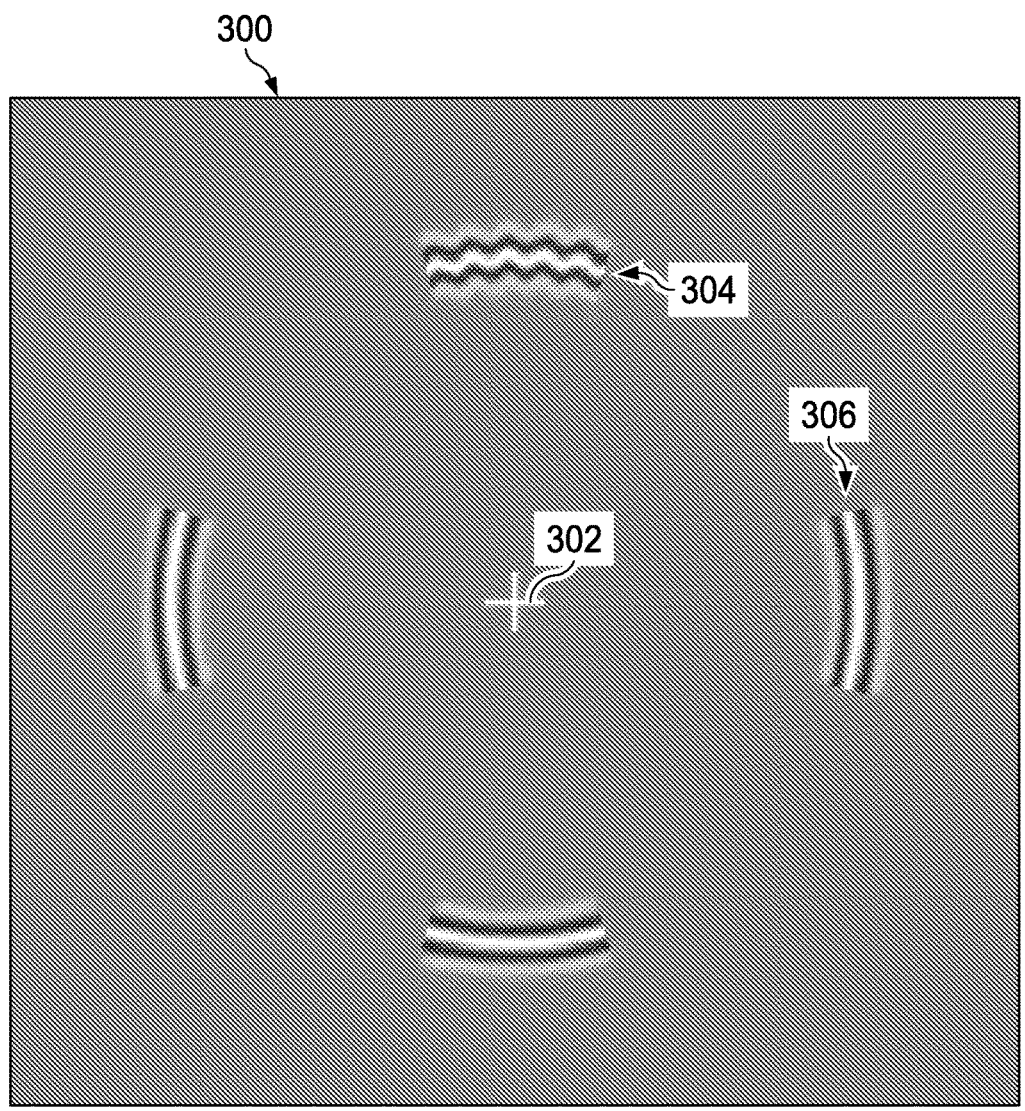
FIG. 4c illustrates another embodiment of a test image including a fixation target and four stimulus patterns.

FIG. 4c shows an embodiment of a test image including a fixation target 302, three smooth arcs 306, and one modulated arc 304. The test image of FIG. 4c is similar to that of FIG. 4b, but the modulated arc 304 has moved to be directly above the fixation target 302 and the modulation amplitude is further reduced.

Figure 4D:
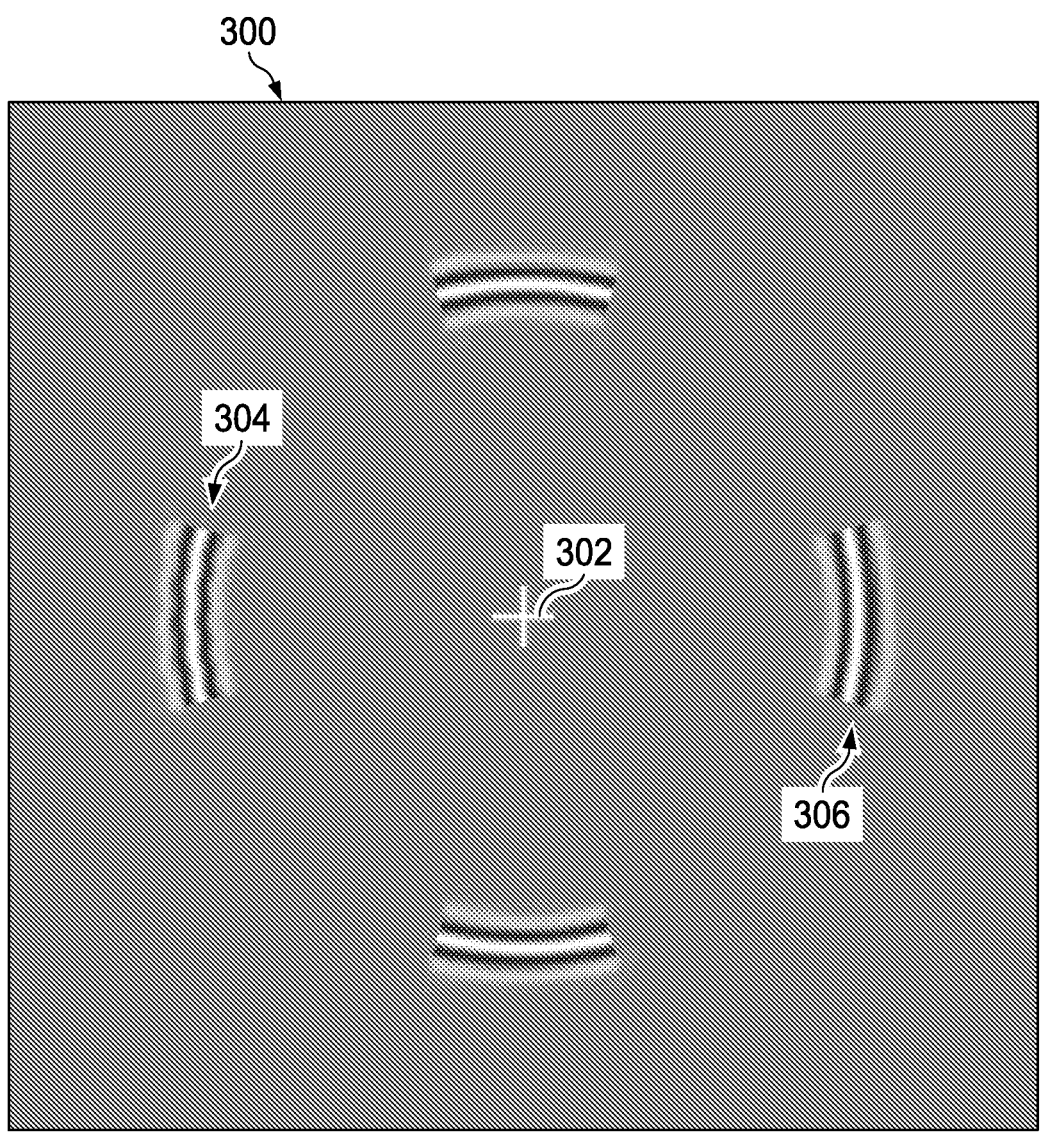
FIG. 4d illustrates another embodiment of a test image including a fixation target and four stimulus patterns.

FIG. 4d shows an embodiment of a test image including a fixation target 302, three smooth arcs 306, and one modulated arc 304. The test image of FIG. 4d is similar to that of FIG. 4c, but the modulated arc 304 has moved to be directly to the left of the fixation target 302 and the modulation amplitude is still further reduced.

Figure 4E:
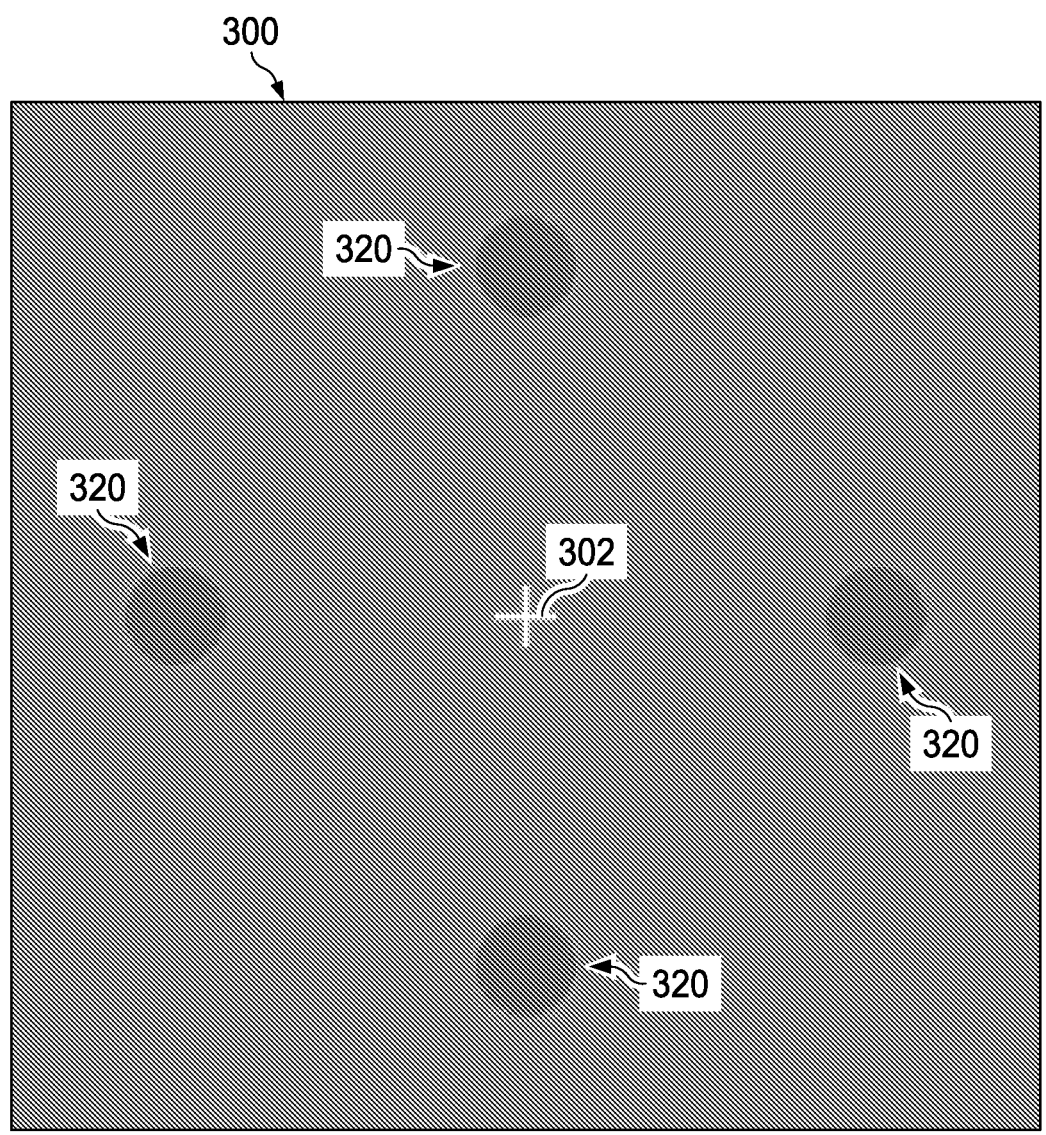
FIG. 4e illustrates an embodiment of a response pattern image suitable for use with the images shown in FIGS. 4a-4d.

FIG. 4e shows an embodiment of a response pattern image suitable for use with the images shown in FIGS. 4a-4d. FIG. 4e includes background 300, fixation target 302, and response targets 320.

Those skilled in the art will recognize that the test images and response pattern image of FIGS. 4a-4e may be used to devise a vision test that is similar to vision tests devised using the images of FIGS. 3a-3e. However, for the case of FIGS. 4a-4e, the stimulus patterns have been rotated by 45 degrees so that stimulation patterns and response targets appear directly above, below, and to the right and left of fixation target 302 (as opposed to being in the lower left, upper left, lower right, and upper right quadrants about fixation target 302). Those skilled in the art will recognize that vision tests may also be implemented that utilize the test images and response images of FIGS. 3a-4e all together and that, with such a test, a greater degree of information can be obtained about the vision function capability of a test subject as a function of where a stimulus pattern falls on their retina. It is noteworthy that combining tests with a coarser division of the visual field and combining patterns, as would be the case for a test combining use of FIGS. 3a-4e, may be beneficial for some embodiments versus developing tests that employ a larger number of regions. Clearly, tests with a larger number of test regions may become confusing to a test subject and make it difficult for visual integration of a test image in a short stimulus interval.

Figure 5:
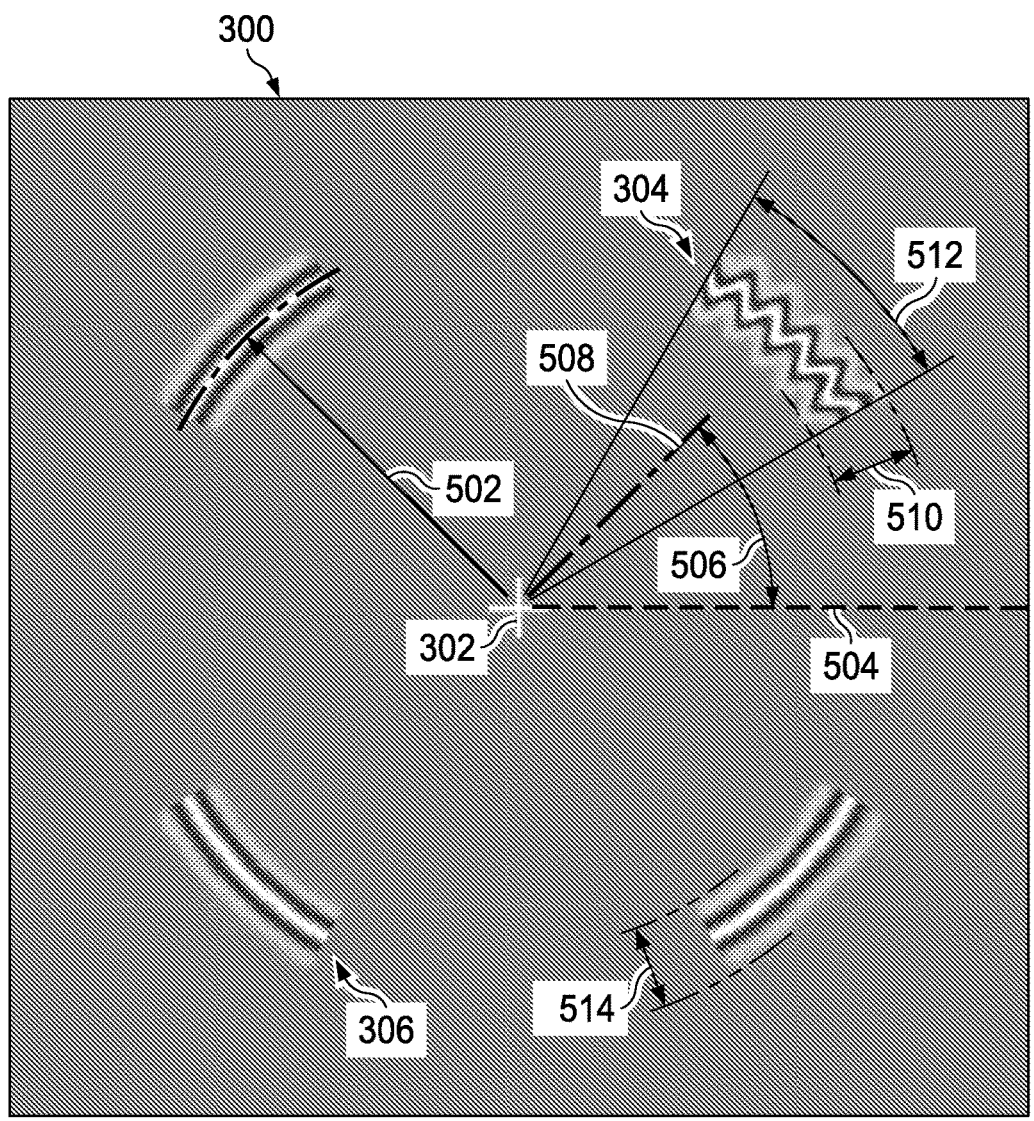
FIG. 5 illustrates another embodiment of a test image including a fixation target and four stimulus patterns.

FIG. 5 shows an embodiment of a test image including a fixation target 302 and four stimulus patterns. Three of the stimulus patterns are smooth arcs 306 and the fourth is a modulated arc 304. FIG. 5 includes dimensions that allow the arc size 512, arc rotational location 506, arc radius 502, modulation amplitude 510, and contour cross-sectional width 514 to be clearly defined. Reference direction 504 points directly to the right of fixation target 302 and arc rotational location 506 is measured counter-clockwise from reference direction 504 to the center of a given arc (or other possible stimulus pattern). Hence, rotational location 506 measures the angle (in degrees, radians, or other convenient measure) from reference direction 504 to arc center line 508 (arc center line 508 is shown as a dashed line in FIG. 5). Arc size 512 measures the length of an arc (in FIG. 5 it is shown measuring the length of modulated arc 304, but the arc size 512 could also be used to measure the length of a smooth arc 306). Arc size 512 could be provided as an angular measure (in degrees, radians, etc.) or as an absolute measure of arc length (in millimeters, inches, etc.), or with other possible measures. Arc radius 502 measures the distance from fixation target 302 to the center of an arc (either a smooth arc 306 as shown or a modulated arc 304). Modulation amplitude 510 measures the peak-to-peak spatial amplitude of the modulation level of modulated arc 304 (in millimeters, inches, or other suitable measurement scale). Contour cross-sectional width 514 measures the width of a smooth contour, such as smooth arc 306 as shown in FIG. 5.

As previously explained, arc size 512, arc rotational location 506, arc radius 502, modulation amplitude 510, and contour cross-sectional width 514 may all be varied to produce a variety of vision test images suitable for testing as described in this patent application. And as previously noted, colors, backgrounds, cross-sectional luminance modulation, shapes, sizes, different numbers of stimulus patterns, stimulus intervals, and other factors that may be applied to various test images may be varied in the course of vision testing for various embodiments.

The benefits of the present disclosure should be clear. It offers techniques to allow for automatic testing of vision function through visual integration of contours distributed about a fixation target. Test images may be presented for a stimulus interval and corresponding response images may be presented for a response interval. A wide variety of test images and response images may be provided in sequence to generate vision tests suitable for analyzing the retinal function of a test subject.

Although the present disclosure has been described in detail, those skilled in the art should understand that they can make various changes, substitutions and alterations herein without departing from the spirit and scope of the invention in its broadest form.

What is claimed is:

1. A method to assess vision function, comprising:
   providing a sequence of test images on a display to a test subject, said display coupled to a computer, during a stimulus interval; and
   providing a response pattern image on said display to said test subject for each of said sequence of test images during a response interval after said stimulus interval;
   wherein:
      each of said sequence of test images includes multiple stimulus patterns arranged around a fixation target;
      said response pattern image includes multiple response targets, each of which corresponds to a location of each of said multiple stimulus patterns;
      at least one of said multiple stimulus patterns differs from others of said multiple stimulus patterns; and
      an assessment of a vision function of said test subject is based at least partially on a selection by said test subject during said response interval, for each of said sequence of test images, of at least one of said multiple response targets of said response pattern image that said test subject indicates corresponds to a location of said at least one of said multiple stimulus patterns that differs from others of said multiple stimulus patterns.

2. The method of claim 1, wherein each of said multiple stimulus patterns include contours with a cross-sectional luminance modulation.

3. The method of claim 2, wherein said cross-sectional luminance modulation includes a central bright region, surrounding dark regions on each side of said central bright region, and outer light regions on outer sides of said surrounding dark regions.

4. The method of claim 1, wherein said others of said stimulus patterns are a smooth arc.

5. The method of claim 1, wherein said at least one of said multiple stimulus patterns is a modulated arc.

6. The method of claim 5, wherein a modulation amplitude of said modulated arc can vary.

7. The method of claim 1, wherein said at least one of said multiple stimulus patterns can be in any quadrant around said fixation point.

8. The method of claim 1, wherein said stimulus interval is typically less than about 250 milliseconds.

9. The method of claim 1, wherein a radius from said fixation target to said multiple stimulus patterns can vary.

10. The method of claim 1, wherein a number of the multiple stimulus patterns can vary.

11. A vision testing system, comprising:
    a display;
    a computer coupled to said display and configured to display to a test subject:
       a sequence of test images during a stimulus interval; and
       a response pattern image for each of said sequence of test images during a response interval after said stimulus interval;
    wherein:
       each of said sequence of test images includes multiple stimulus patterns arranged around a fixation target;
       said response pattern image includes multiple response targets, each of which corresponds to a location of each of said multiple stimulus patterns;
       at least one of said multiple stimulus patterns differs from others of said multiple stimulus patterns; and
       an assessment of a vision function of said test subject is based at least partially on a selection by said test subject during said response interval, for each of said sequence of test images, of at least one of said response patterns of said response pattern image that said test subject indicates corresponds to a location of said at least one of said multiple stimulus patterns that differs from others of said multiple stimulus patterns.

12. The vision testing system of claim 11, wherein each of said multiple stimulus patterns include contours with a cross-sectional luminance modulation.

13. The vision testing system of claim 12, wherein said cross-sectional luminance modulation includes a central bright region, surrounding dark regions on each side of said central bright region, and outer light regions on outer sides of said surrounding dark regions.

14. The vision testing system of claim 11, wherein each of said others of said stimulus patterns is a smooth arc.

15. The vision testing system of claim 11, wherein said at least one of said multiple stimulus patterns is a modulated arc.

16. The vision testing system of claim 15, wherein a modulation amplitude of said modulated arc can vary.

17. The vision testing system of claim 15, wherein an arc length of said multiple stimulus patterns can vary.

18. The vision testing system of claim 11, wherein said stimulus interval is typically less than about 250 milliseconds.

19. The vision testing system of claim 11, wherein said stimulus patterns can be greyscale or color.

20. The vision testing system of claim 11, wherein a background for said multiple stimulus patterns can be greyscale or color.

* * * * *